United States Patent [19]

Kleis et al.

[11] Patent Number: 4,961,339
[45] Date of Patent: Oct. 9, 1990

[54] DEVICE FOR TESTING ARTICLES OF CLOTHING FOR WATERPROOFNESS

[75] Inventors: Rudolf Kleis; Gerd Ziegler, both of Putzbrunn, Fed. Rep. of Germany

[73] Assignee: W. L. Gore & Associates, Inc., Newark, Del.

[21] Appl. No.: 365,150

[22] Filed: Jun. 12, 1989

[30] Foreign Application Priority Data

Jun. 13, 1988 [DE] Fed. Rep. of Germany ....... 3826275

[51] Int. Cl.$^5$ .................... G01N 17/00; G01N 27/06
[52] U.S. Cl. ........................................ 73/73; 73/866.4
[58] Field of Search ......................... 73/73, 336, 866.4

[56] References Cited

U.S. PATENT DOCUMENTS

| 2,839,644 | 6/1958 | Ohlheiser | 73/73 X |
| 3,886,791 | 6/1975 | Grossman | 73/865.6 X |
| 4,194,041 | 3/1980 | Gore et al. | 2/82 X |
| 4,432,223 | 2/1984 | Paquette et al. | 73/866.4 X |
| 4,655,235 | 4/1987 | Scott, Jr. | 73/865.6 X |

FOREIGN PATENT DOCUMENTS

| 0138825 | 11/1979 | Fed. Rep. of Germany | 73/866.4 |
| 0153138 | 9/1984 | Japan | 73/866.4 |

Primary Examiner—Daniel M. Yasich
Attorney, Agent, or Firm—Gary A. Samuels

[57] ABSTRACT

A device according to the invention for testing articles of clothing has a carrier on which the article of clothing to be tested can be placed and then sprayed with water. The carrier is an imitation human body or part of a body with moisture sensors on it surface which are connected to an analyzer.

2 Claims, 8 Drawing Sheets

Fig. 1
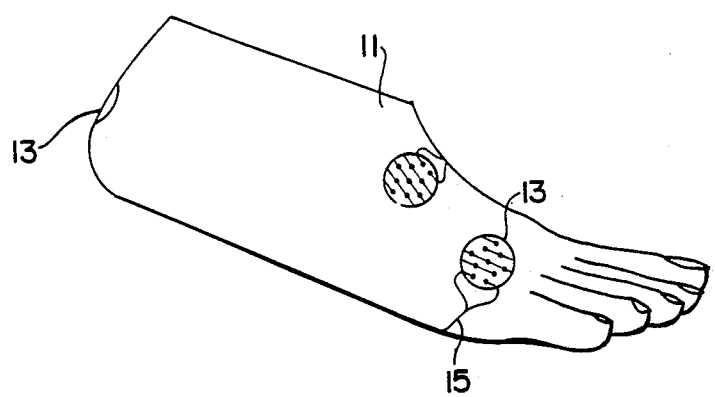
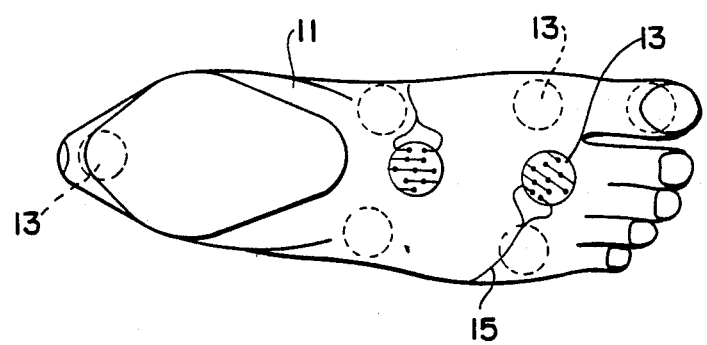
Fig. 2

DEVICE FOR TESTING ARTICLES OF CLOTHING FOR WATERPROOFNESS

FIELD OF THE INVENTION

The invention relates to a device for testing articles of clothing for waterproofness.

BACKGROUND OF THE INVENTION

Recently, an increasing number of articles of clothing, such as shoes, boots, gloves, coats, jackets and pants, have been manufactured as waterproof clothing. This clothing often does not have a waterproof outer layer but is lined with a waterproof, water vapor-permeable function layer which is supposed to prevent moisture reaching the inside or inner lining of the clothing.

Although this type of clothing is supposed to be waterproof, there are often places which are not waterproof. This is usually caused by processing errors or manufacturing methods which cause water permeability while the clothing is being made. Frequently, water bridges are formed between the outside and the inside of the function layer or the inner lining of the clothing by means of seam holes or seam threads. Also, threads or pieces of cloth which are not properly trimmed and therefore project over the cut ends of the function layer frequently result in water bridges. This causes water to collect on the inside of the clothing then seep into the lining. For example, these water bridges cause the inner lining of waterproof shoes to become damp shortly after the outside of the shoe becomes wet.

So far, the so-called PFI tester of the Testing and Research Institute of the Shoe Industry has been used to test shoes for waterproofness. This testing device consists of a steel shoe tree which is formed like shoe tree in the toe area only, and otherwise is shaped like a narrow strap. This steel shoe tree is designed with a spring-loaded joint in the flex area of the shoe, i.e. where a fold forms during walking at the base of the toes. This enables the shoe tree-like tip to be raised against the spring force and returned to its resting position. For this purpose, the shoe to be tested, which is pulled over the shoe tree, is placed with its heel on a stationary steel plate and with its toe area on a movable steel plate. This steel plate is moved in a way which has both a horizontal and a vertical component. This requires an expensive mechanism which is submerged in the water bath, which is especially corrosive due to the tannic acid discharged from the shoes to be tested, attacks the mechanism and eventually damages it.

Moreover, the steel shoe tree known in the art, which is shaped like a narrow steel strap or steel rod up to the toe of the shoe, only comes in contact with the shoe in two places of realtively small area. Due to pressure from the base plate, this steel shoe tree moves in the shoe. At the support points between the steel shoe tree and shoe, a chafing or rubbing of the lining and thus of the waterproof function layer can occur. if moisture is detected in the shoe, it is difficult to determine whether it has penetrated due to a chafed function layer or due to water bridges caused by the system or during manufacture.

In the shoe tester known in the art, the test for waterproofness is carried out by looking at and feeling the shoe removed from the shoe tree. Frequently, filter paper is placed in the removed shoe in order to possibly determine the presence of penetrated water. The number of cycles at which the service person stops the shoe tester, removes the shoe from the water and examines the inside of the shoe for penetrated moisture is purely coincidental.

The shoe tester known in the art is only designed for testing a very specific shoe size. If a shorter shoe tree for a smaller shoe were placed on the clamp, the base plate which moves up and down would no longer be in the proper place under the toe area of the small shoe. Correspondingly, the opposite applies to a shoe which is larger than the one stipulated for the shoe tester.

Other waterproof articles of clothing, such as gloves, jackets, pants and coats, should also be tested for waterproofness. So far, it has not been possible to test these articles of clothing in their entirety. Only a section of material from an article of clothing to be tested has been loaded with a water column of defined height and tested for waterproofness. So far, it has not been possible to determine how entire articles of clothing behave when they are worn and where the particularly sensitive places are located.

One purpose this invention is to make available a device for testing articles of clothing for waterproofness which provides a high degree of measurement accuracy, reliability and expressiveness in a situation which simulates actual use as closely as possible.

SUMMARY OF THE INVENTION

A device for testing articles of clothing for waterproofness, which comprises a carrier on which the article of clothing to be tested can be placed, said carrier having, a plurality of moisture sensors on the surface of the carrier positioned in the places where the article of clothing is prone to penetration of water, said sensors being connected to an analyser which is activated if the moisture sensor connected to it indicates the presence of moisture.

In a preferred embodiment, the activation of the analyser is caused by two electrodes at a predetermined distance from each other which are electrically bridged by penetrated moisture, thus creating a current flow which can be evaluated by the analyser.

BRIEF DESCRIPTION OF THE DRAWINGS

FIG. 1 is a side view of an artifical foot used as a shoe carrier with moisture sensors on its surface;

FIG. 2 is a top view of the artifical foot shown in FIG. 1;

DESCRIPTION OF THE INVENTION

Figure 3:
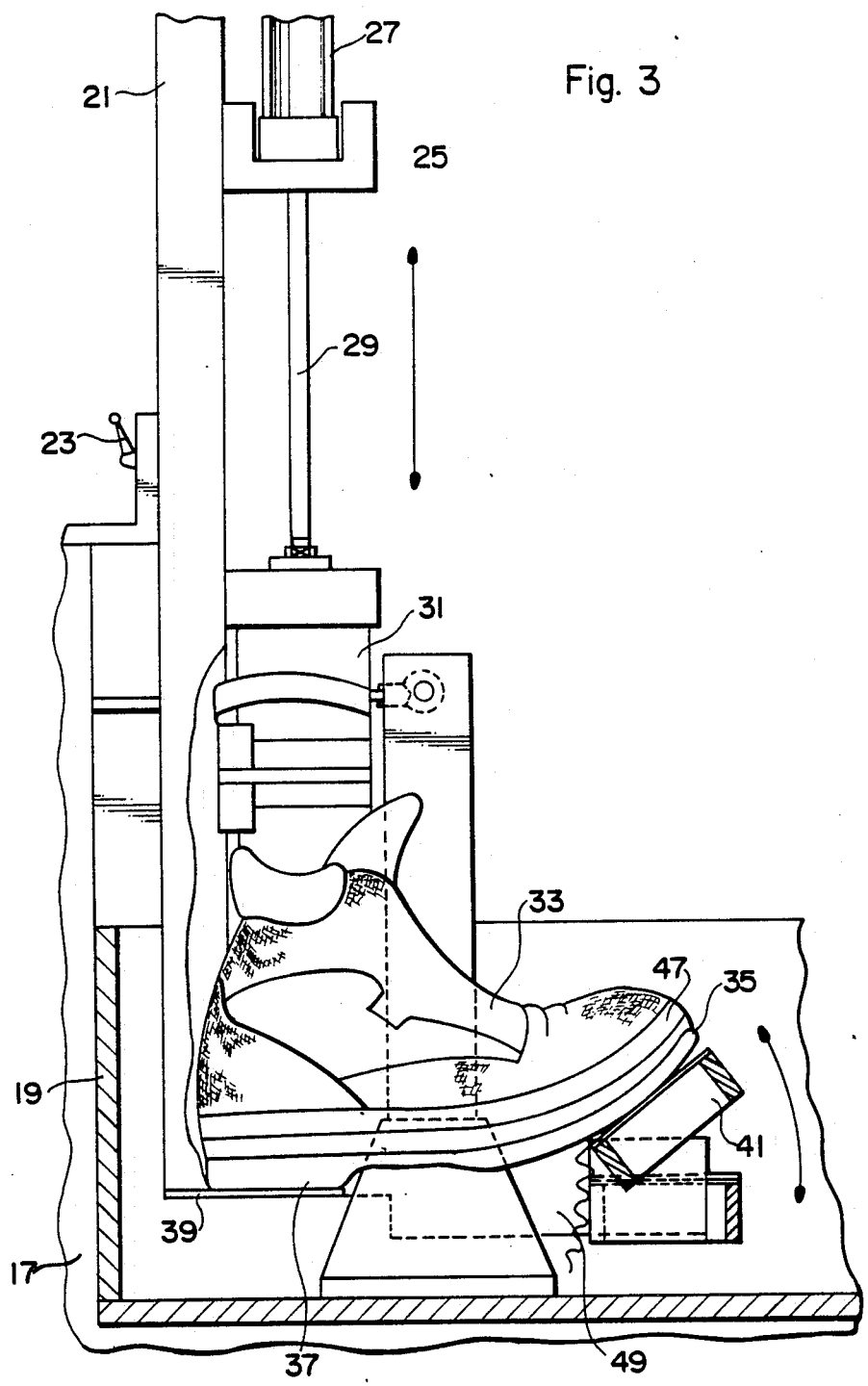
FIG. 3 is a schematic representation of a shoe tester according to the invention in side view.

Due to the fact that according to the invention the surface of the carrier, which can, for example, be a shoe tree, a glove tree or a dummy, has moisture sensors in various places, the waterproofness test can be carried out without repeatedly removing the article of clothing from the carrier in order to determine whether moisture has already penetrated to the inside. Since the evaluation takes place automatically while the article of clothing is on the carrier, the precise point at which the moisture penetrates to the inside can be accurately indicated and recorded. Since the criterion of dry or wet is decided on the basis of the initial signal of the moisture sensors, the waterproofness test can be stopped automatically as soon as a moisture sensor indicates the presence of moistrue without requiring a service person. the length of the test and/or number of movement cycles until a moisture sensor indicates the presence of moisture can be measured or counted automatically. After it has been started up, the test device requires no further attention. If a testing device is used which has several carriers, for example a shoe tester with several imitation feet or artificial feet which are measured and evaluated independently of each other, the testing device can be left alone to run for hours or even days and then the test results can simply be read off for the individual articles of clothing. When one considers that, in a shoe tester, waterproof shoes, for example, are subjected to several hundred thousand or even a million movement cycles before the end of a test, one can imagine the savings in manpower. In contrast, in the shoe tester known in the art the test must be frequently interrupted and the shoe removed from the shoe tree to examine it for penetrated moisture in order to be able to determine with at least some accuracy the point at which the moisure seeped through to the inside. There must also be at least one service person present during almost the entire test.

In the case of articles of clothing such as jackets, coats and pants, it would be very expensive to examine all the areas of the article of clothing which have proven, according to the invention, to be particularly prone to the penetration of moisture with the water column test known in the art. Areas which have not been recognized as sensitive in a particular manufacturing method would remain unexamined in the water column test known in the art. However, if the testing device according to the invention is used in the form of a dummy equipped with moisture sensors, any number of moisture sensors can be attached to any place on the dummy so that a jacket or coat can be tested for the penetration of moisture at as many places as desired.

In particularly preferable way, the dummy or parts of it can be made inflatable to ensure particularly good application of the moisture sensors to the inside of the article of clothing to be tested.

It is particularly advantageous if the dummy with the article of clothing to be tested is placed in a shower stall which as a number of shower heads in various positions, so that the article of clothing can essentially be sprayed with water from all sides at the same time.

The testing device is especially easy to read and simple to handle if it has an indicator which gives the shape of the article of clothing to be tested and is equipped with luminous elements, perferably luminous diodes, at the places which correspond to the positions of the individual moisture sensors on the carrier. This makes it possible to see at a glance the place on the article of clothing to be tested which is not waterproof.

The design of a shoe tester will be considered with the aid of FIGS. 1 through 5.

An imitation foot in the form of an artificial foot (11) is used for the shoe tester of the invention, at least the from part of which consists of a flexible material. This makes it possible for the shoe placed on the artificial foot (11) to execute a rolling movement which can correspond to a great extent to the rolling movement of a real foot during walking.

There are moisture sensors (13) at different places on the surface of the artificial foot (11) which are connected to an electric analyzer by means of electrical wires (15).

As FIG. 2 in particular shows, the individual moisture sensors (13) are mainly arranged in places where a shoe is usually subjected to particular pressure or bending strain, such as in the flex area at the base of the toes and at various places on the foot sole. A moisture sensor is also placed under the open end of the big toe since this area of the shoe is subjected to relatively great stress during walking. In addition, there is at least one moisture sensor (13) in the area of the shoe tongue in order to determine whether this area, which is prone to water bridges, remains dry.

The testing device consists essentially of a clamping device for the shoe to be tested, a driving unit for the walking motion, a water bath and an electrical control with indicator. The mechanical part of the testing device will now be described in greater detail with the aid of FIG. 3.

A water bath (19) and a guide (21) which can be adjusted vertically to the stand (17) are arranged on the stand (17). In order to adjust the height of the guide (21), a screw lever (22) is released and after the new vertical position is set, the guide (21) is screwed in again. The guide (21) has a mount (25) for a pneumatic cylinder (27). The pneumatic cylinder has a movable clamp bar (29) at whose open end there is a clamp (31) and at whose other end the artificial foot, which cannot be seen in FIG. 3, is secured. The shoe (33) to be tested for waterproofness is placed on the artificial foot (11) which has a sole (35) and a heel (37). The heel (37) is placed on a flat surface (39) which is connected with the guide (21). The toe area of the sole (35) lies on a step (41) which can be moved up an down in a circular motion in order to simulate the rolling movement which occurs at the toe of the shoe (33) during walking.

Figure 4:
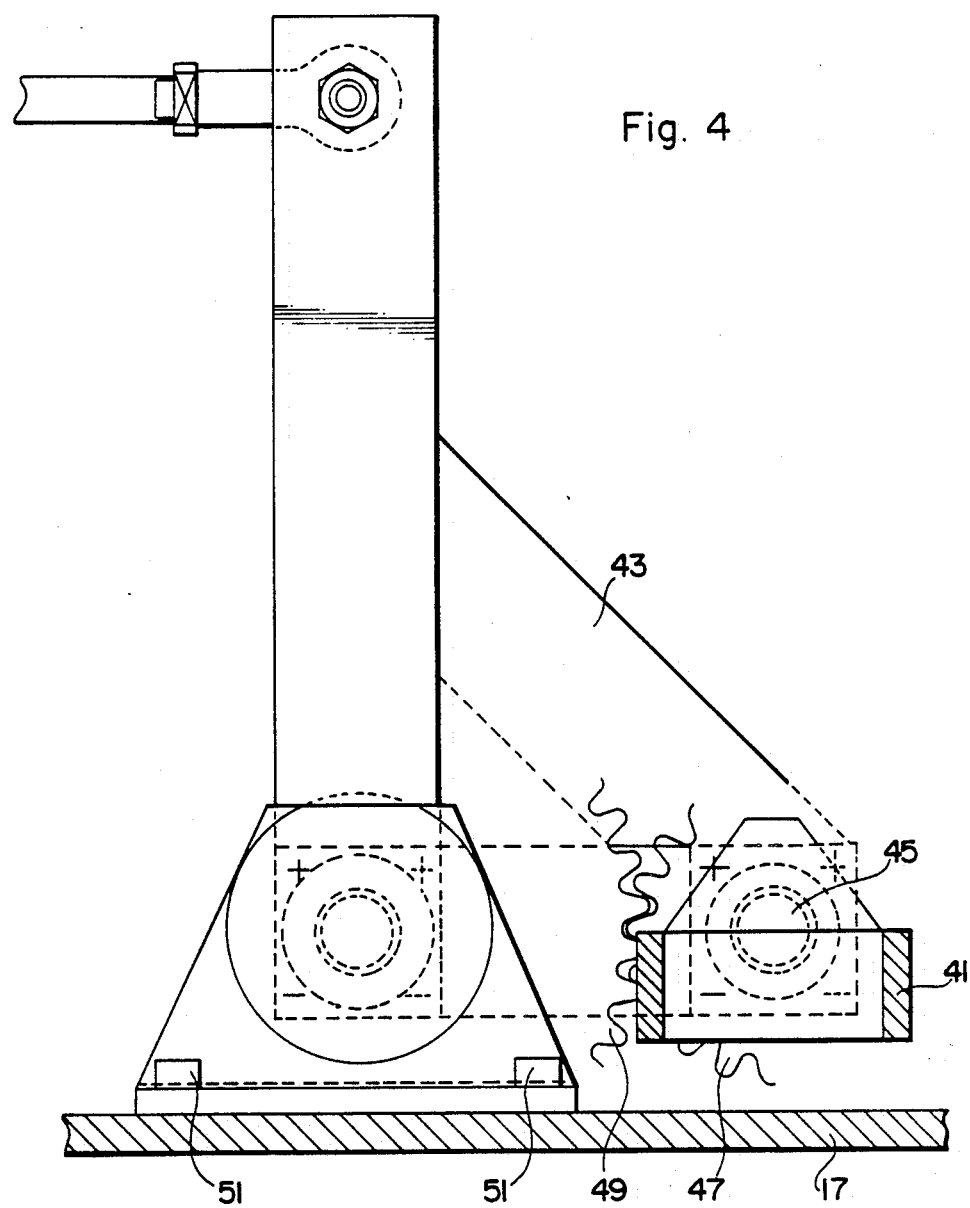
FIG. 4 is a schematic representation of the shoe movement mechanism of the shoe tester presented in FIG. 3.

The movement mechanism of the step (41) can be clearly seen from FIG. 4. This movement mechanism consists of a lever (43) which is raised and lowered by a crank drive of a motor with adjustable speed. The step (41) is attached, so that it can be twisted, to the lower end of the lever (43) by means of a horizontal rotating shaft (45). There is also a gear wheel (47) on the rotating shaft (45) which can be moved along with the step (41) around the rotating shaft (45). The gear wheel (47) mates with a segment of the gear wheel (49) which is secured by means of screws (51) to the floor of the stand (17). During the up and down movement of the lever (43), the gear wheel (47) mates with the gear wheel segment (45) in a rolling movement. Thus, the step executes a curved up and down movement. As a result of the combined rotation and the up and down movement of the step (41), the shoe (43) on the step (41) executes a rolling movement which closely simulates that which occurs during walking.

By arranging a crank drive, a lever (43), a gear wheel (47) and a gear wheel segment (49) on both longitudinal ends of the step (41), a long step (41) can be manufactured on which there is room for a number of shoes side by side. This results in a preferred design in which a number of independent guides (21) are arranged along the step (41), each with a mount (25), a pneumatic unit (27, 29), a clamp (31), an artificial foot (11) and a flat surface (39). The moisture sensors (13) of each artificial foot are connected separably to an analyzer with an indicator by means of an electric plug and socket connection and a flat cable. Due to the fact that the height of the guides (21) can be adjusted, any testing unit can be adjusted to the heel height of the shoe (33) or boot to be tested with this testing unit in such a way that the toe (35) always lies appropriately on the step (41).

Moreover, any guide (21) can be adjusted in the longitudinal direction of the shoe (not shown). This makes it possible to adjust the testing unit to any length of show desired in such a way that the toe (35) always lies appropriately on the step (41).

In this type of testing device, the height of any guide (21) can be individually adjusted in order to test a number of shoes at the same time. Moreover, each flat surface (39) can be individually adjusted in the longitudinal direction of the shoe. Every testing unit assigned to a shoe (33) can be independently lowered or raised by means of its pneumatic unit (27, 29). Each testing unit has its own indicator and its own movement cycle counter. As soon as a moisture sensor (13) indicates the presence of water in a testing unit, the shoe in question (33) is lifted out of the water bath by raising the appropriate clamp rod (29) by means of the pneumatic cylinder (27). Then the indicator can be read to determine which of the test unit's moisture sensors indicated the presence of moisture and where on the movement cycle counter the moisture was indicated.

Figure 5:
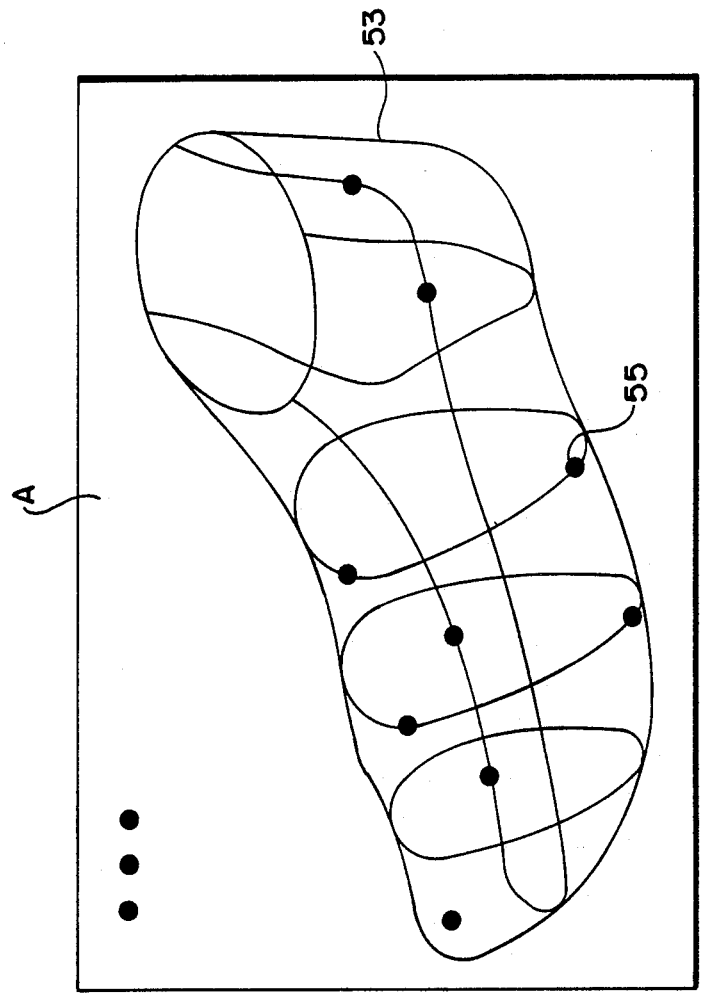
FIG. 5 is an example of an indicator for a shoe tester.

An example of the indicator for each testing unit is presented in FIG. 5. In accordance with this, each indicator has a schematic representation (53) of an artificial foot, whereby luminous diodes (55) are placed at the sites which correspond to the moisture sensors. As soon as a moisture sensor (13) indicates the presence of moisture, the appropriate luminous diode (55) lights up. Therefore, the place at which water penetrated the tested shoe (33) can be seen at a glance.

A preferred design for a testing device for articles of clothing such as jackets, pants, coats and overalls is presented in FIGS. 6 through 9. A dummy (63) of realistic proportions with a number of moisture sensors (13) attached to its surface is placed in a shower stall. These sensors are primarily located at sites which are particularly prone to the penetration of water. These are the shoulder area, the stomach area, where there are often zippers which cause problems with respect to waterproofness, the crotch area, the upper thigh and knee area and the shin area. On the ceiling (67) of the shower stall (61) there are several shower heads (69) which are located at different places with respect to the dummy (63) and can be aimed so that they direct water in different directions.

Figure 7:
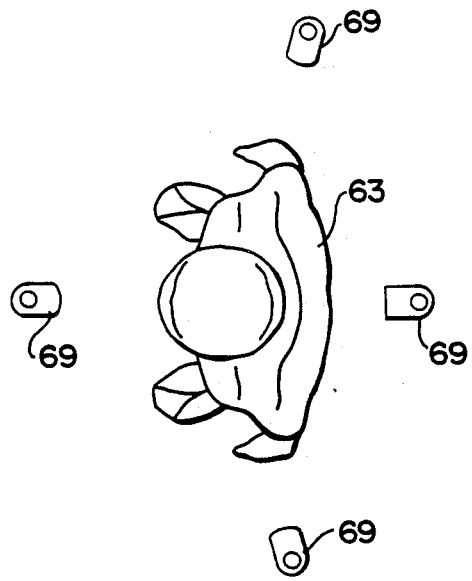
FIG. 7 is a top view of the dummy presented in FIG. 6 showing the distribution of shower heads.

The spatial distribution of the shower heads (69) with respect to the dummy (63) is presented schematically in FIG. 7, which shows a top view of the dummy (63).

Figures 8, 9:
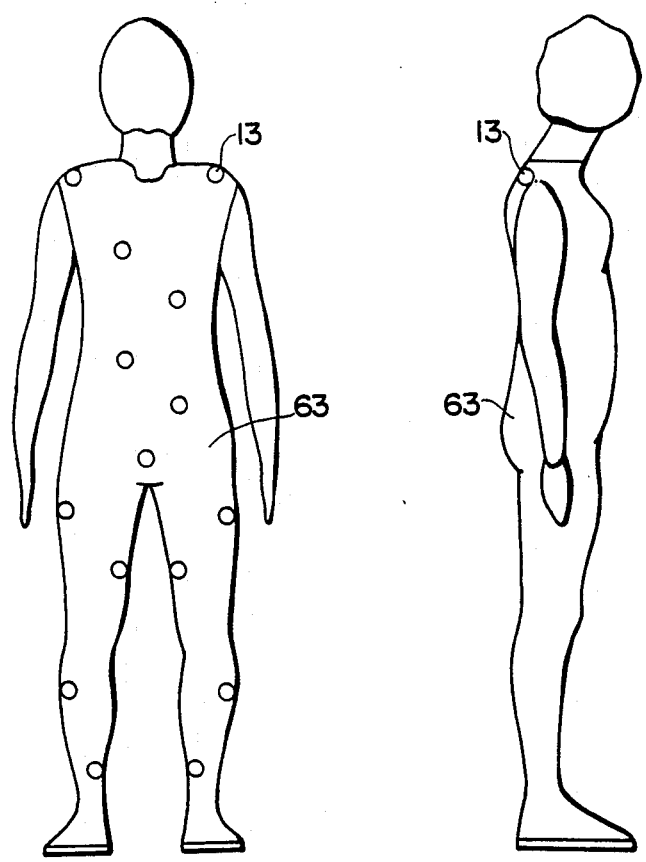
FIG. 8 is a schematic rear view of the dummy with moisture sensors presented in FIG. 6.
FIG. 9 is a lateral view of the dummy presented in FIG. 8.

FIG. 8 presents the rear view of the dummy (63) indicating the places at which moisture sensors (13) are preferably located. FIG. 9 presents a lateral view of a dummy indicating the preferred position for moisture sensors (13) attached to the back shoulder area. In a particularly preferred design, the dummy is at least partially inflatable. This makes it possible to ensure that the moisture sensors (65) in the inflatable area are flush against the inside of the article of clothing to be tested.

Figure 10:
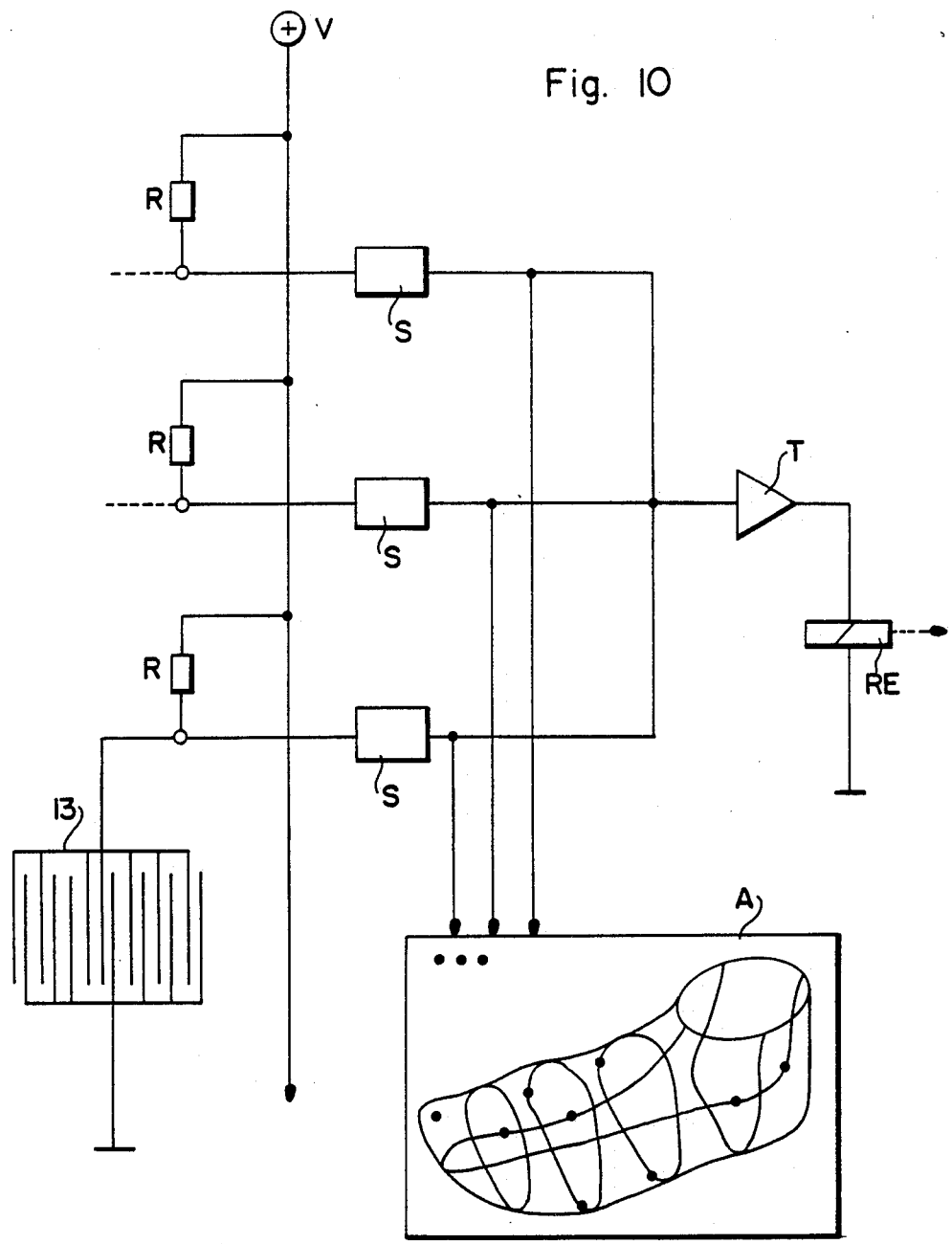
FIG. 10 is an electrical block diagram of the analyzer of a testing device according to the invention.

A simplified, electrical block diagram for an analyzer connected to several moisture sensors is presented in FIG. 10. This presents a simplified diagram of the connections for only three moisture sensors (13), although the carrier of a testing device of the invention may have more sensors. In so doing, just the lower sensor (13) is presented, while the connecting wires for the two upper sensors are indicated only by means of a broken line. The moisture sensors (13) are connected by means of an accompanying series resistor R to a common power source V, on the one hand, and to an earth point, on the other. The connecting points between the individual series resistors and the accompanying moisture sensors are connected to a threshold switch whose points are jointly connected with a relay driver (T) whose outlet controls a relay (RE).

In the design example shown in FIG. 10, the moisture sensor (13) has a number of electrodes which mesh together, whereby adjacent electrodes are connected to different poles of the current supply source. In a completely dry state, no current flows between the electrodes poled against each other. If moisture penetrates the article of clothing being tested and reaches a moisture sensor (13), electricity is conducted between the electrodes opposite each other and a current flows through the accompanying series resistor (R) due to the electrical conductance of water. In turn, this results in a change in the electrical potential at the inlet of the accompanying threshold switch (S). If the flow of current through the moisture sensor (13) and thus the change in potential at the inlet of the threshold switch (S) exceeds a certain threshold value, the output signal of the threshold switch (S) causes the relay (RE) to respond by means of the drive amplifier (T). In the case of a shoe tester, the shoe in which the presence of water has been detected is raised out of the water bath with the aid of the accompanying pneumatic unit (27), (29), and the movement cycle counter which is assigned to this shoe stops. Moreover, the indicator (A) shows which moisture sensor indicated the presence of moisture by means of the appropriate luminous diode.

The moisture sensors (13) preferably consist of two parallel and branched copper electrodes which are manufactured in an etching procedure. This type of moisture sensor suffers if current flows through it while it is wet. Therefore, in a preferred design, the current flows through the moisture sensors (13) is also interrupted by activation of the relay (RE). In order for the indicator (A) to determine which of the moisture sensors (13) responded, the relay (RE) also holds the indicator pattern. This reading and the counting position of the movement cycle counter can be held and displayed as long as desired, until the beginning of a new test, for example.

Figure 6:
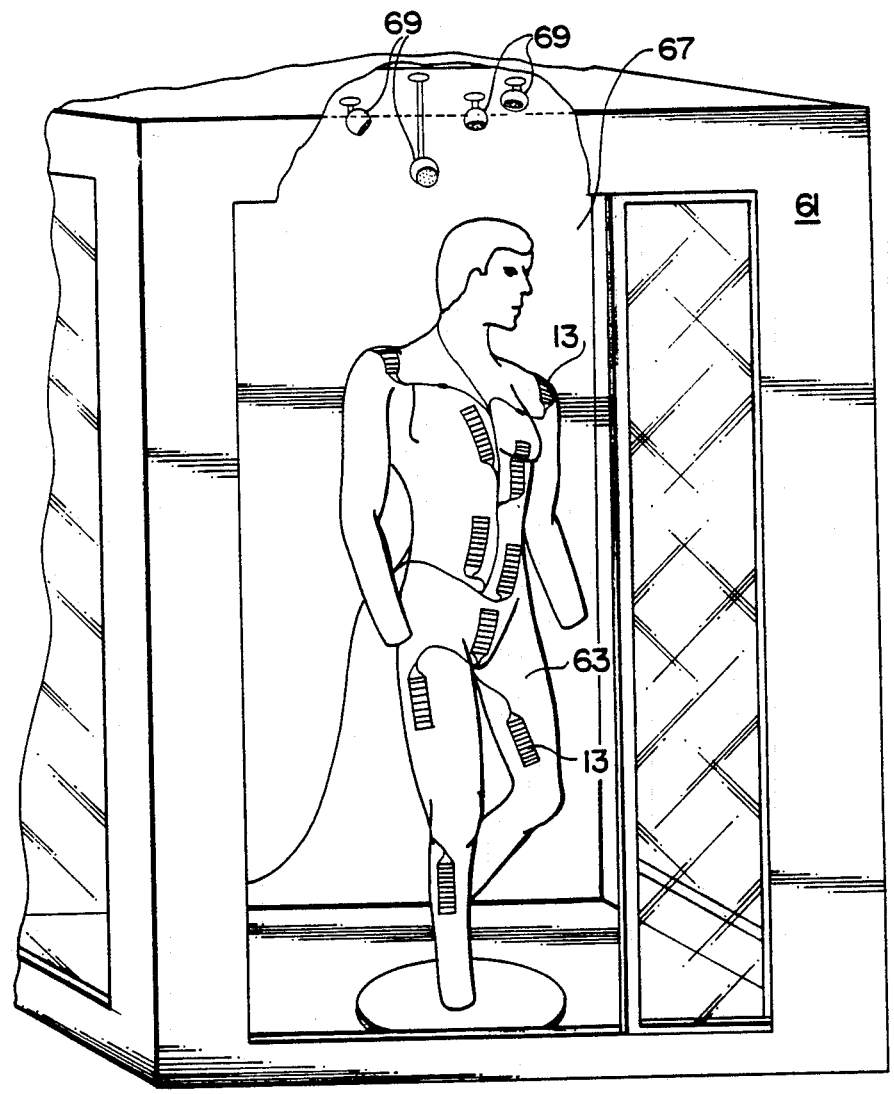
FIG. 6 is a schematic representation of a dummy epuipment with moisture sensors which is placed in a shower stall.

In the case of a testing device, as is shown in FIG. 6, the flow of shower water is cut off by activation of the relay (RE). In the same way as the shoe tester, the reading on the indicator (A) and the test time determined by the test length measuring device are held and displayed until they are no longer needed, due to the start of a new test, for example.

We claim:

1. A device for testing articles of clothing for waterproofness, which comprises a carrier adapted to support an article of clothing to be tested, said carrier having essentially the same shape as a human body, said carrier having a plurality of moisture sensors on the surface of the carrier, positioned in places where the article of clothing is prone to penetration of water, said sensors being connected to an analyzer which is activated if a moisture sensor of said sensors connected to it indicates the presence of moisture; said activation of the analyzer being caused by at least one pair of electrodes of said moisture sensor at a predetermined distance from each other which are electrically bridged by penetrated moisture, thus creating a current flow which can be evaluated by the analyzer.

2. A device for testing articles of clothing for waterproofness, which comprises a flexible artifical hand adapted to support an article of clothing to be tested said hand having a plurality of moisture sensors on the surface of the hand, positioned in places where the article of clothing is prone to penetration of water, said sensors being connected to an analyzer which is activated if a moisture sensor of said sensors connected to it indicates the presence of moisture; said activation of the analyzer being caused by at least one pair of electrodes of said moisture sensor at a predetermined distance from each other which are electrically bridged by penetrated moisture, thus creating a current flow which can be evaluated by the analyzer.

* * * * *